(12) United States Patent
Galambos McLaughlin

(10) Patent No.: US 9,326,739 B2
(45) Date of Patent: May 3, 2016

(54) MAMMOGRAM TABLE

(71) Applicant: Cheryl A. Galambos McLaughlin, Pittsgrove, NJ (US)

(72) Inventor: Cheryl A. Galambos McLaughlin, Pittsgrove, NJ (US)

(*) Notice: Subject to any disclaimer, the term of this patent is extended or adjusted under 35 U.S.C. 154(b) by 0 days.

(21) Appl. No.: 14/263,863

(22) Filed: Apr. 28, 2014

(65) Prior Publication Data
US 2015/0305693 A1 Oct. 29, 2015

(51) Int. Cl.
*A61B 6/04* (2006.01)
*A61B 6/00* (2006.01)

(52) U.S. Cl.
CPC .............. *A61B 6/0435* (2013.01); *A61B 6/502* (2013.01); *A61B 6/0407* (2013.01)

(58) Field of Classification Search
CPC ...... A61B 6/04; A61B 6/0407; A61B 6/0414; A61B 6/0421; A61B 6/0435; A61B 5/055; A61B 5/0555; A61B 6/502; A61B 6/50; A61G 7/018; A61G 7/012; A61G 7/005; A61G 7/002; A61G 13/06; A61G 13/04; A61G 13/02
USPC ...................... 5/601, 600, 735, 731, 611, 610; 378/208, 209, 37, 204
See application file for complete search history.

(56) References Cited

U.S. PATENT DOCUMENTS

| | | | | |
|---|---|---|---|---|
| 3,302,022 A * | 1/1967 | Brenner et al. | ................ | 378/179 |
| 3,868,103 A * | 2/1975 | Pageot et al. | ....................... | 5/614 |
| 3,981,492 A * | 9/1976 | Hallmann | .......................... | 5/601 |
| 4,195,829 A * | 4/1980 | Reser | ................................ | 5/614 |
| 4,856,741 A * | 8/1989 | Schaefer | ..................... | 248/122.1 |
| 5,437,280 A | 8/1995 | Hussman | | |
| 5,564,438 A * | 10/1996 | Merchant | .......................... | 5/613 |
| 5,855,554 A * | 1/1999 | Schneider et al. | ............. | 600/407 |
| 6,298,114 B1 | 10/2001 | Yoda | | |
| 6,419,390 B1 | 7/2002 | Landis-Lowell | | |
| 6,651,279 B1 * | 11/2003 | Muthuvelan | ....................... | 5/600 |
| 6,857,147 B2 * | 2/2005 | Somasundaram | ................ | 5/601 |
| 6,883,194 B2 * | 4/2005 | Corbeil | ................ | A61B 5/0091 378/37 |
| 6,886,198 B2 * | 5/2005 | Marin | ................... | A61B 5/0091 378/209 |
| 6,986,179 B2 * | 1/2006 | Varadharajulu et al. | ........... | 5/611 |
| 7,000,271 B2 * | 2/2006 | Varadharajulu | .................... | 5/610 |
| 7,028,356 B2 * | 4/2006 | Somasundaram | ................ | 5/607 |
| 7,125,167 B2 * | 10/2006 | Alakkat | ......................... | 378/209 |
| 7,186,024 B2 * | 3/2007 | Varadharajulu | ................ | 378/209 |
| 7,621,007 B2 * | 11/2009 | Somasundaram | ................ | 5/607 |
| 7,864,918 B2 * | 1/2011 | Schilling et al. | ................. | 378/37 |
| 7,881,427 B2 * | 2/2011 | Kalender et al. | ................ | 378/37 |
| 7,945,019 B2 | 5/2011 | Kalender et al. | | |
| 7,957,503 B2 | 6/2011 | Kobayashi | | |

(Continued)

FOREIGN PATENT DOCUMENTS

| | | |
|---|---|---|
| WO | 2012032308 | 3/2012 |
| WO | 2012068373 | 5/2012 |

*Primary Examiner* — Robert G Santos
(74) *Attorney, Agent, or Firm* — Superior IP, PLLC; Dustin L. Call

(57) ABSTRACT

A mammogram table for supporting a patient during a breast examination. The mammogram table includes a platform configured to support a patient while lying in a prone position during a breast examination and a pedestal configured to bear the platform and the patient during the breast examination. The mammogram table also includes a breast template configured to position the breasts of the patient during a breast examination and a mounting bracket configured to allow imaging equipment to be attached to the mammogram table. The mammogram table further includes a breast support configured to receive the breasts of the patient.

15 Claims, 5 Drawing Sheets

(56) References Cited

U.S. PATENT DOCUMENTS

| | | |
|---|---|---|
| 7,961,840 B2 * | 6/2011 | Ohi et al. .................. 378/37 |
| 8,102,964 B2 * | 1/2012 | Schilling et al. ............ 378/37 |
| 2004/0088791 A1 * | 5/2004 | Corbeil ............ A61B 5/0091 5/601 |
| 2004/0098804 A1 * | 5/2004 | Varadharajulu et al. ....... 5/611 |
| 2004/0111801 A1 * | 6/2004 | Marin ............... A61B 5/0091 5/621 |
| 2004/0172145 A1 * | 9/2004 | Varadharajulu ............. 700/60 |
| 2004/0172756 A1 * | 9/2004 | Somasundaram ............ 5/600 |
| 2004/0172757 A1 * | 9/2004 | Somasundaram ............ 5/601 |
| 2004/0172758 A1 * | 9/2004 | Alakkat ...................... 5/610 |
| 2005/0084074 A1 * | 4/2005 | Varadharajulu ............. 378/209 |
| 2005/0114996 A1 * | 6/2005 | Somasundaram ............ 5/601 |
| 2008/0021478 A1 * | 1/2008 | Wolford ..................... 606/80 |
| 2009/0211584 A1 | 8/2009 | Savich |
| 2010/0080344 A1 * | 4/2010 | Schilling et al. ............ 378/37 |
| 2010/0080345 A1 * | 4/2010 | Schilling et al. ............ 378/37 |
| 2010/0080346 A1 * | 4/2010 | Kalender et al. ............ 378/37 |
| 2010/0080350 A1 * | 4/2010 | Kalender et al. ............ 378/37 |
| 2010/0128843 A1 * | 5/2010 | Tita ......................... 378/37 |
| 2010/0322379 A1 * | 12/2010 | Ohi et al. .................. 378/37 |
| 2015/0305693 A1 * | 10/2015 | Galambos McLaughlin ........ A61B 6/04 5/601 |

* cited by examiner

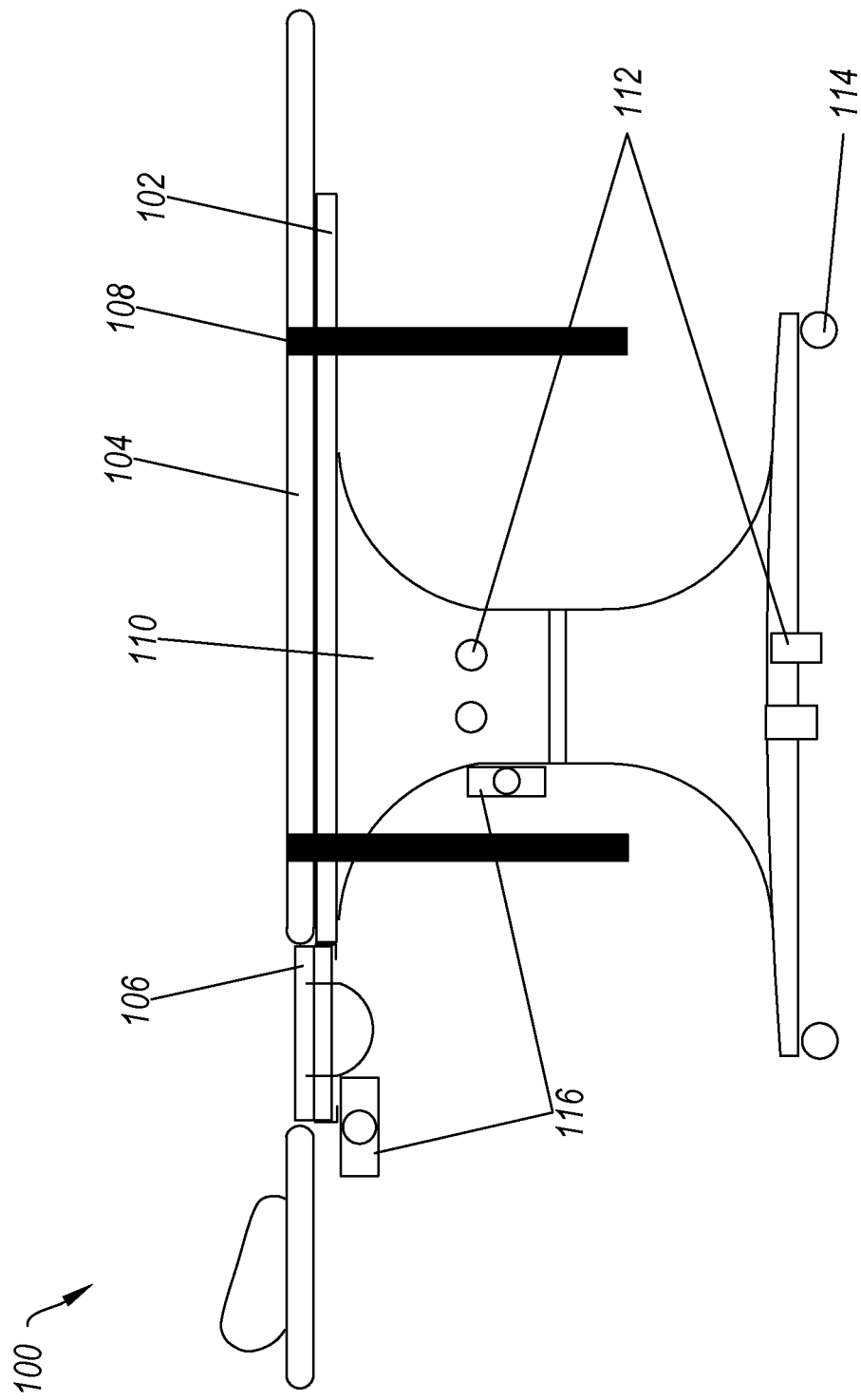

MAMMOGRAM TABLE

CROSS-REFERENCE TO RELATED APPLICATIONS

Not applicable.

BACKGROUND OF THE INVENTION

Screening exams and are used to detect cancer and other diseases. For example, a mammogram may be obtained to perform a breast cancer screening exam. If an abnormality is detected during the screening exam then a biopsy may be recommended (a stereotactic procedure).

There are many devices available which immobilize the breasts during examination. However, these devices tend to either deform the breast and/or cause patient discomfort. I.e., the devices are uncomfortable for the patient during use. This discourages women undergoing breast exams. That is, because the experience is unpleasant it no doubt leads to fewer breast examinations than would otherwise occur.

Nevertheless, these devices must be used to prevent inaccurate results. This means that medical personnel tend to perform the examinations as quick as possible in order to minimize patient discomfort. However, attempting to perform the examination more quickly may lead to errors. I.e., the examination may be performed to quickly to be accurate.

Accordingly, there is a need in the art for a device which can immobilize the breasts of a patient during a breast examination. Moreover, there is a need in the art for the device to be comfortable for the patient.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes a mammogram table for supporting a patient during a breast examination. The mammogram table includes a platform configured to support a patient while lying in a prone position during a breast examination and a pedestal configured to bear the platform and the patient during the breast examination. The mammogram table also includes a breast template configured to position the breasts of the patient during a breast examination and a mounting bracket configured to allow imaging equipment to be attached to the mammogram table. The mammogram table further includes a breast support configured to receive the breasts of the patient.

Another example embodiment includes a mammogram table for supporting a patient during a breast examination. The mammogram table includes a platform configured to support a patient while lying in a prone position during a breast examination and a pedestal configured to bear the platform and the patient during the breast examination. The mammogram table also includes a control configured to allow the height of the platform to be adjusted and a breast template configured to position the breasts of the patient during a breast examination. The mammogram table further includes a mounting bracket configured to allow imaging equipment to be attached to the mammogram table and a breast support configured to receive the breasts of the patient.

Another example embodiment includes a mammogram table for supporting a patient during a breast examination. The mammogram table includes a platform configured to support a patient while lying in a prone position during a breast examination and a pedestal configured to bear the platform and the patient during the breast examination. The mammogram table also includes a control configured to allow the height of the platform to be adjusted and one or more casters configured to allow the mammogram table to be moved as desired. The mammogram table additionally includes a pad covering at least a portion of the platform configured to cushion the patient during the breast examination and a breast template configured to position the breasts of the patient during a breast examination. The mammogram table further includes one or more straps configured to ensure that the patient remains in position during the breast examination and a mounting bracket configured to allow imaging equipment to be attached to the mammogram table. The mammogram table moreover includes a breast support configured to receive the breasts of the patient and a bracket configured to attach the breast support to the breast template.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1A illustrates a side view of the example of a mammogram table;

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1B:
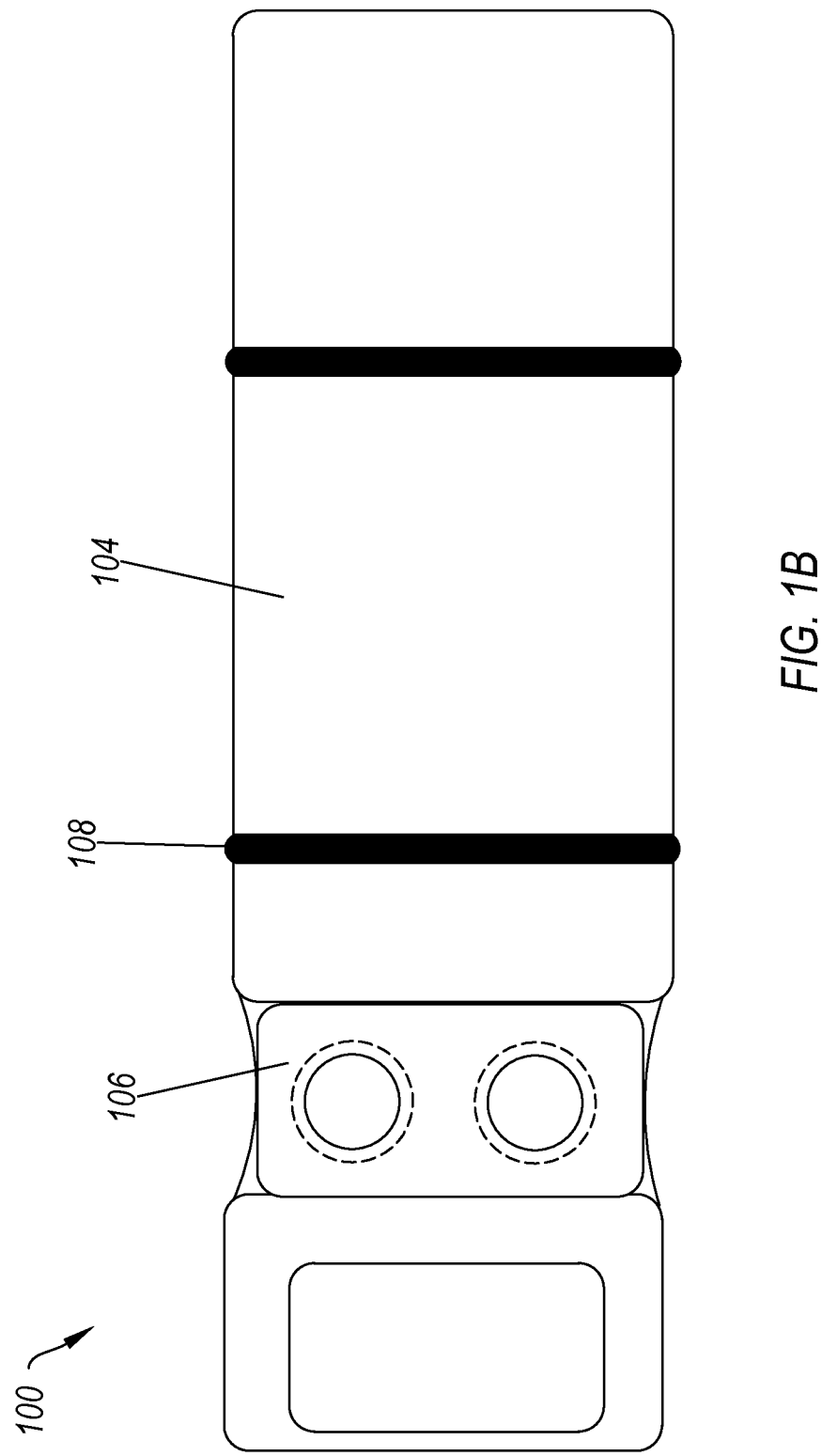
FIG. 1B illustrates a top view of the example of a mammogram table.

FIGS. 1A and 1B (collectively "FIG. 1") illustrate an example of a mammogram table 100. FIG. 1A illustrates a side view of the example of a mammogram table 100; and FIG. 1B illustrates a top view of the example of a mammogram table 100. The mammogram table 100 positions a patient while a breast examination, such as a mammogram, an underarm examination, an imaging scan, such as an MRI, ultrasound or x-ray, or any other imaging breast examination, is performed. In particular, the mammogram table 100 allows a patient to lie prone and positions the patient's breasts, maximizing patient comfort while the breast examination is performed.

FIG. 1 shows that the mammogram table 100 can include a platform 102. The platform 102 acts as a surface on which the patient may lie in the prone position. I.e., the platform 102 is configured to support the body of the patient during the breast examination. The platform 102 can be of sufficient size to support the entire body of the patient. E.g., the platform 102 can be approximately 30 inches wide and 70 inches long, allowing the platform 102 to support the patient from head to toe. In addition, the platform 102 can be made of any material that is able to support the body of the patient. For example, the platform 102 can be made of steel or any other material of sufficient strength. As used in the specification and the claims, the phrase "configured to" denotes an actual state of configuration that fundamentally ties recited elements to the physical characteristics of the recited structure. As a result, the phrase "configured to" reaches well beyond merely describing functional language or intended use since the phrase actively recites an actual state of configuration. In addition, as used in the specification and the claims, the term approximately shall mean that the value is within 10% of the stated value, unless otherwise specified.

FIG. 1 also shows that the mammogram table 100 can include a pad 104. The pad 104 is placed on the top of the platform 102 and serves as a cushioning device for the patient. For example, the pad 104 may include visco-elastic polyurethane "memory" foam and other types of foam. Memory foam is advantageous because it provides comfort but is also relatively thin when compressed under the weight of the patient, which can be helpful because the patient's breast must extend sufficiently below the table for the breast examination to be performed. Additionally or alternatively, the pad 104 may include one or more foam layers having different characteristics. For example, the pad 104 includes multiple foam pads. For example, foam pads covering the distal end sections (where the patient's head and feet will be located) may be permanently attached to the table top with a removable pad placed over the central section of the platform 102. E.g., the pad 104 can include a pillow, foot or leg pads or any other desired supports.

FIG. 1 further shows that the mammogram table 100 can include a breast template 106. The breast template 106 positions the breasts of the patient during a breast examination. The breast template 106 can be changed to accommodate different patients. I.e., the breast template 106 can be attached to or removed from the platform 102 depending on the needs of the patient. For example, the breast template 106 can include different amounts of padding, accommodate different breast sizes, etc. Additionally or alternatively, the breast template 106 can accommodate attachment of different parts that allow the breast template 106 to be customized for each patient, as described below.

FIG. 1 moreover shows that the mammogram table 100 can include one or more straps 108. The straps 108 are configured to secure the patient. I.e., the one or more straps 108 can ensure that the patient remains in the correct position during the examination. The straps 108 can include hook and loop fasteners (Velcro), buckles or any other mechanism for securing the straps 108 in place during use.

FIG. 1 also shows that the mammogram table 100 can include a pedestal 110. The pedestal 110 bears the platform 102. I.e., the platform 102 rests in part on the pedestal 110, with a portion of the platform 102 not directly above the pedestal 110. This allows the medical examination to proceed unobstructed by the pedestal 110. The pedestal 110 can include an adjustment mechanism which allows the height and angle of the platform 102 to be adjusted as desired. For example, the adjustment mechanism can include a motor and/or hydraulics.

FIG. 1 further shows that the mammogram table 100 can include a control 112. The control 112 can allow a medical professional to adjust the height and/or angle of the platform 102. I.e., the platform 102 can be raised, lowered or tilted as needed to accommodate the patient. For example, the platform 102 can be lowered to allow the patient to lie down or get up and can be raised during the examination. The control 112 can include buttons, foot pedals, a remote or any other desired control 102. One of skill in the art will appreciate that the control 112 can include multiple control mechanisms. For example, the control 112 can include buttons and foot pedals if so desired.

FIG. 1 additionally shows that the mammogram table 100 can include locking casters 114. The casters 114 allow the mammogram table 100 to be moved as desired. I.e., the casters 114 allow the mammogram table 100 to be positioned where desired so that the examination can be performed. Further, the casters 114 can be locked to prevent undesired movement of the mammogram table 100.

FIG. 1 moreover shows that the mammogram table 100 can include a mounting bracket 116. The mounting bracket 116 can allow imaging equipment to be mounted underneath the platform 102. For example, the imaging equipment can include MRI, ultrasound, x-ray or any other desired imaging equipment. The mounting bracket 116 can ensure that the imaging equipment is placed in the correct location relative to the breasts of the patient. The mounting bracket 116 may be movable relative to the platform 102. I.e., the mounting bracket 116 may allow the imaging equipment to be moved relative to the breasts of the patient, allowing imaging from different angles.

Figure 2:
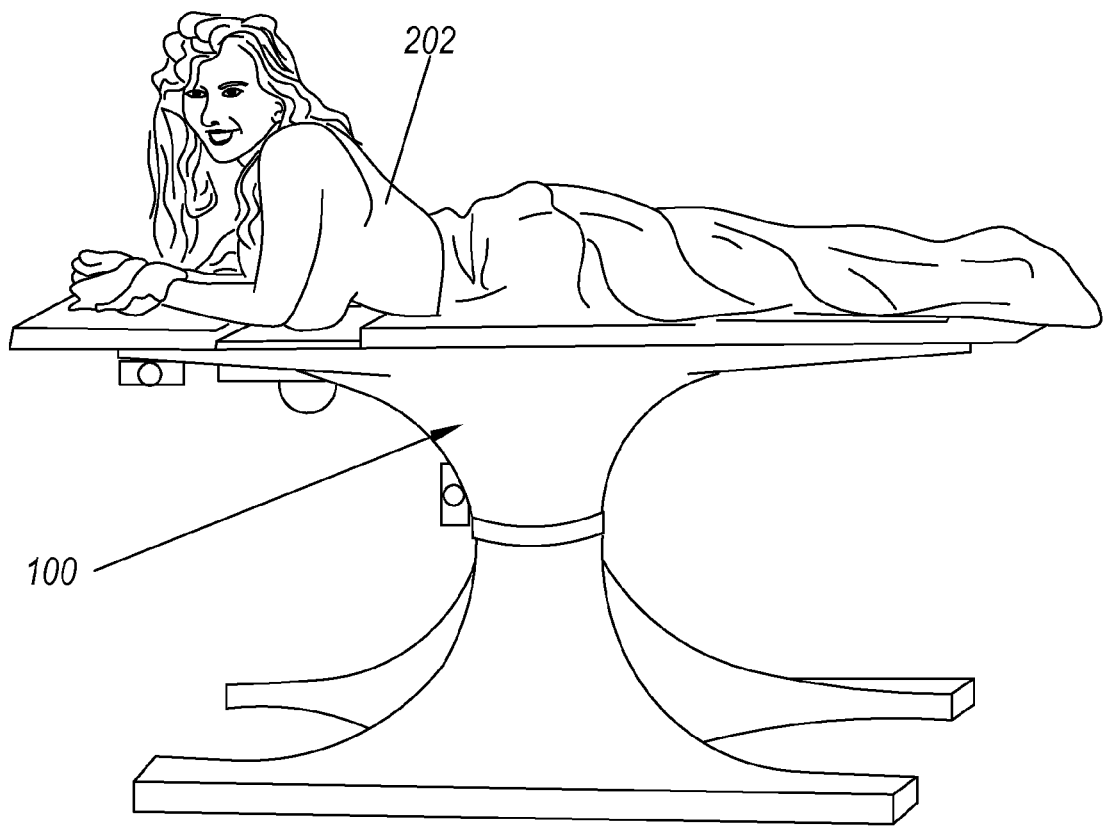
FIG. 2 illustrates an example of a patient on a mammogram table.

FIG. 2 illustrates an example of a patient 202 on a mammogram table 100. The patient 202 lays prone on the mammogram table 100 allowing for a breast examination. In particular, the breasts of the patient 202 are aligned to allow for a breast examination including a mammogram, an underarm examination, an imaging scan, such as an MRI, ultrasound or x-ray, a biopsy, or any other desired breast examination. The mammogram table 100 maximizes the comfort of the patient during the breast examination.

Figure 3A:
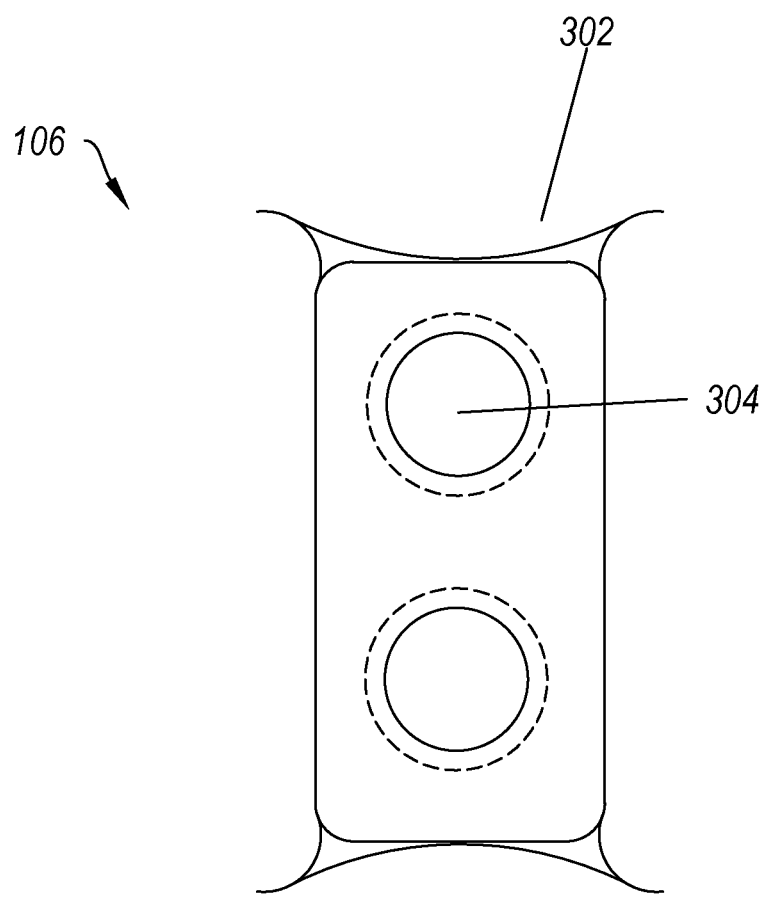
FIG. 3A illustrates a top view of the example of a breast template.
Figure 3B:
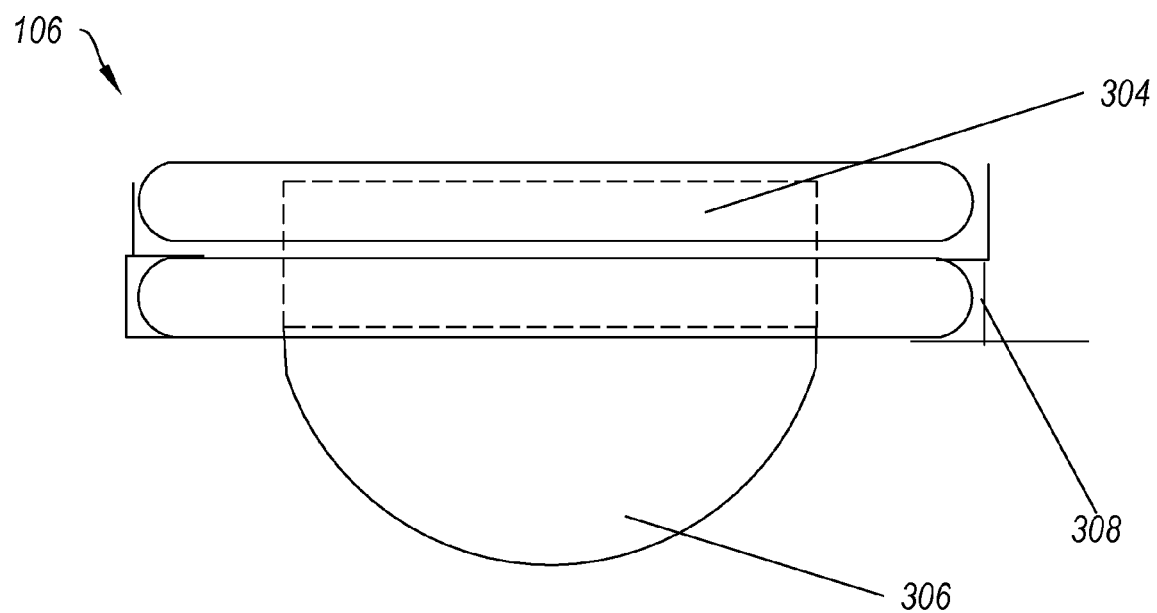
FIG. 3B illustrates a side view of the example of a breast template.

FIGS. 3A and 3B (collectively "FIG. 3") illustrate an example of a breast template 106. FIG. 3A illustrates a top view of the example of a breast template 106; and FIG. 3B illustrates a side view of the example of a breast template 106. The breast template 106 includes one or more openings which position the breasts of the patient for a breast examination. I.e., the breast template 106 ensures that the patient's breasts remain in the correct position for a breast examination. This is critical to ensure that the examination may be performed quickly and produce accurate results.

FIG. 3 shows that the breast template 106 can include a cutout 302. The cutout 302 is an area of the breast template 106 which is configured to allow for an underarm examination. I.e., the breast template 106 is sized to just support the patient to allow for an underarm examination when the patient places her arms in the correct position. An underarm examination includes checking the armpits and sides of the breasts for lumps or other irregularities.

FIG. 3 also shows that the breast template 106 can include an aperture 304. The aperture 304 allows the breasts of the patient to extend through the platform 102. I.e., the aperture 304 includes one or more openings through which the patient's breasts will pass, allowing the examination to proceed. Additionally or alternatively, the aperture 304 can be configured to receive a breast support, as described below. In particular, the aperture 304 can be sized to accommodate the breasts of the patient.

FIG. 3 further shows that the breast template 106 can include a breast support 306. The breast support 306 is configured to support the breasts of the patient during the breast examination. For example, the breast support can be interchangeable, allowing the patient's breasts to be fully supported during the entirety of the examination. E.g., the breast support 306 can be sized according to breast cup sizes. The breast support 306 is transparent with respect to the imaging equipment. I.e., the breast support 306 includes material that does not affect the imaging equipment during use or can be "eliminated" by the imaging equipment, allowing for imaging of the breasts. The breast support 306 can be cup shaped. I.e., the breast support 306 can be a paraboloid (3D parabola) with an opening configured to receive the patient's breasts. Additionally or alternatively, there may be a slit in breast support 306 to allow insertion of a sheet of film for x-ray imaging.

FIG. 3 additionally shows that the breast template 106 can include a bracket 308. The bracket 308 can be configured to attach the breast support 306 to the breast template 106. For example, the bracket 308 can be "L" shaped. I.e., there can be a portion that extends perpendicularly from the breast template 106 and then include a 90 degree bend. The breast support 306 can then be slid into the bracket 308, positioning the breast support 306 directly below the aperture of the breast template 106.

One of skill in the art will appreciate that the breast support 306 can be attached to the breast template 106 in any desired manner. For example, the breast support 306 can be placed on top of the breast template 106 with the breast support 306 extending through the aperture of the breast template 106. I.e., the breast support 306 can be supported by, but not permanently attached to, the breast template 106.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A mammogram table for supporting a patient during a breast examination, the mammogram table comprising:
    platform configured to support a patient while lying in a prone position during a breast examination;
    a pedestal configured to bear the platform and the patient during the breast examination;
    a control configured to allow the height and angle of the platform to be adjusted;
    one or more casters configured to allow the mammogram table to be moved as desired;
    a pad covering at least a portion of the platform configured to cushion the patient during the breast examination;
    a breast template, wherein the breast template:
        is configured to support the chest of the patient and position the breasts of the patient during a breast examination; and
        includes:
            an aperture configured to allow the breasts of the patient to pass through the breast template;
            an arm cutout, wherein the arm cutout is configured to provide access to the armpit of the patient while the breast template is configured to support the chest of the patient in the prone position when receiving an underarm examination;
    one or more straps configured to ensure that the patient remains in position during the breast examination;
    a mounting bracket configured to allow imaging equipment to be attached to the mammogram table;
    a left breast support configured to receive the left breast of the patient, wherein the left breast support:
        includes:
            a cup configured to support the left breast of the patient;
            an opening to receive the left breast of the patient; and
            a lip near the opening; and
    a right breast support configured to receive the right breast of the patient, wherein the right breast support:
        includes:
            a cup configured to support the right breast of the patient;
            an opening to receive the right breast of the patient; and
            a lip near the opening; and
    a bracket, wherein the bracket is:
    is mounted on the underside of the breast template; and
    is configured to attach the breast supports to the underside of the breast template such that the openings of the breast supports are aligned with the aperture of the breast template.

2. The mammogram table of claim 1, wherein each breast support is transparent with regard to the imaging equipment.

3. The mammogram table of claim 1, wherein each breast support is sized according to the breast size of the patient.

4. The mammogram table of claim 1, wherein each breast support is a paraboloid.

5. The mammogram table of claim 1, wherein the bracket is "L" shaped.

6. The mammogram table of claim 1, wherein the mounting bracket is configured to allow the imaging equipment to be moved relative to the platform.

7. The mammogram table of claim 1, wherein the control is further configured to allow the angle of the platform to be adjusted.

8. The mammogram table of claim 1, wherein the control is further configured to allow the angle of a portion of the platform to be adjusted.

9. The mammogram table of claim 1, wherein the control includes one or more foot pedals.

10. The mammogram table of claim 1, wherein the control includes one or more buttons.

11. The mammogram table of claim 1, wherein the one or more straps each include a fastener.

12. The mammogram table of claim 11, wherein the fastener includes a buckle.

13. The mammogram table of claim 11, wherein the fastener includes a hook and loop fastener.

14. The mammogram table of claim 1, wherein the bracket allows lateral movement of the left breast support relative to the right breast support.

15. The mammogram table of claim 1, wherein the bracket allows lateral movement of the left breast support and the right breast support to match the width between the breasts of the user.

* * * * *